(12) United States Patent
Geng et al.

(10) Patent No.: US 11,513,109 B2
(45) Date of Patent: Nov. 29, 2022

(54) BIOLOGICAL TOXICITY TEST METHOD FOR EVALUATING THE ECOLOGICAL SAFETY OF ADVANCED OXIDATION PROCESSES

(71) Applicant: NANJING UNIVERSITY, Nanjing (CN)

(72) Inventors: Jinju Geng, Nanjing (CN); Yingying Fu, Nanjing (CN); Xingsheng Gao, Nanjing (CN); Hongqiang Ren, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 675 days.

(21) Appl. No.: 16/016,606

(22) Filed: Jun. 24, 2018

(65) Prior Publication Data

US 2019/0271676 A1 Sep. 5, 2019

(30) Foreign Application Priority Data

Mar. 2, 2018 (CN) .......................... 201810173567.7

(51) Int. Cl.
| | | |
|---|---|---|
| *G01N 33/18* | (2006.01) | |
| *C12Q 1/26* | (2006.01) | |
| *C12Q 1/28* | (2006.01) | |
| *C12Q 1/30* | (2006.01) | |

(52) U.S. Cl.
CPC ............ *G01N 33/186* (2013.01); *C12Q 1/26* (2013.01); *C12Q 1/28* (2013.01); *C12Q 1/30* (2013.01); *G01N 33/1826* (2013.01); *G01N 2333/908* (2013.01); *G01N 2333/90283* (2013.01)

(58) Field of Classification Search
CPC ............. G01N 33/186; G01N 33/1826; G01N 2333/90283; G01N 2333/908; C12Q 1/26; C12Q 1/28; C12Q 1/30; C02F 1/32; C02F 1/72; C02F 1/30; C02F 1/722
See application file for complete search history.

(56) References Cited

FOREIGN PATENT DOCUMENTS

CN          103616489 A    *  3/2014

OTHER PUBLICATIONS

Shu et al., Water Research, 2016, 101: 157-166 (Year: 2016).*
Kumar et al., Pesticide Biochemistry and Physiology, 2011, 99: 45-52 (Year: 2011).*

(Continued)

*Primary Examiner* — Allison M Fox
*Assistant Examiner* — Qing Xu
(74) *Attorney, Agent, or Firm* — Dragon Sun Law Firm, PC; Jinggao Li; Nathaniel Perkins (57) ABSTRACT

A biological toxicity test method for evaluating an ecological safety of an advanced oxidation process comprising the following steps: (1) collecting (preparing) a waste water to be determined; (2) collecting the waste water and a tap water after the advanced oxidation process treatment; (3) subjecting Koi (*Cyprinus carpio haematopterus*) to the water after treatment for exposure to poison; (4) Determining an anti-oxidation enzyme activity of a liver of the Koi after exposure; (5) Data analyzing. By comparing the changes of liver enzyme activities in different water, the present method evaluates the toxicity changes of micro-pollutant containing water before and after treatment, which fills in the gap of the ecological risk assessment for advanced oxidation technology.

4 Claims, 10 Drawing Sheets

(56) References Cited

OTHER PUBLICATIONS

Yan et al., Hubei Agricultural Science, 2013, vol. 52, No. 11, pp. 2616-2617 (Year: 2013).*
Koi Wikipedia printout, downloaded from the website of https://en.wikipedia.org/wiki/Koi on Apr. 2, 2021 (Year: 2021).*
Kang et al., Ecotoxicology and Environmental Safety, 2010, 73:1449-1455. (Year: 2010).*
Koi-species profile printout, downloaded on Nov. 6, 2021 from the USGS website: https://nas.er.usgs.gov/queries/FactSheet.aspx?SpeciesID=3294 (Year: 2016).*
Google translation of Yan et al., Hubei Agricultural Science, 2013, vol. 52, No. 11, pp. 2616-2617.*
Singh et al., Water Research, 2015, 71:257-273.*
Zhang et al., Chemical Engineering Journal, 2016, 302:526-534.*
Deng et al., Curr. Pollution Rep., 2015, 1: 167-176.*

\* cited by examiner

BIOLOGICAL TOXICITY TEST METHOD FOR EVALUATING THE ECOLOGICAL SAFETY OF ADVANCED OXIDATION PROCESSES

CROSS-REFERENCE TO RELATED APPLICATIONS

This application claims priority to Chinese Patent Application No. 201810173567.7 with a filing date of Mar. 2, 2018. The content of the aforementioned application, including any intervening amendments thereto, are incorporated herein by reference.

TECHNICAL FIELD

The invention relates to the technical field of environmental toxicology, and in particular to a biological toxicity test method for evaluating the ecological safety of advanced oxidation processes.

BACKGROUND TECHNIQUE

Over the past decades, research on environmental contaminants has shifted from traditional contaminants (polychlorinated biphenyls, polycyclic aromatic hydrocarbons) to new micro-contaminants, of which pharmaceuticals and personal care products (PPCPs) are a new type of pollutant that is widely concerned. PPCPs include a variety of human and animal medicines, disinfectants, perfumes and personal care products (detergents, shower gels, sunscreens, etc.). Because the process in existing waste water treatment plant is not designed to remove this new type of contaminants, the removal rate of PPCPs in the waste water treatment process is low, so the exhaust water from the waste water plant becomes one of the major sources of PPCPs in the environmental water bodies. PPCPs has inherent feature of strongly persistence, biologically activity, bioaccumulation, and difficult to biodegradation, and therefore have long-term potential risks to human health and ecosystems. The current research on the ecotoxicity and environmental risk of PPCPs shows that PPCPs have a harmful effect on the normal physiological functions of aquatic fish and damage the vulture kidney through the food chain. In view of the fact that PPCPs are difficult to remove by conventional waste water treatment methods and are widely found in environmental waters, many scientists have developed various advanced oxidation processes to remove such contaminants that are difficult to biodegrade. Advanced oxidation technology can effectively remove contaminants through strong oxidative free radicals.

In fact, the refractory organics produce intermediate products during the advanced oxidation process, and these intermediates cannot be completely removed. Therefore, the mineralization rate of organic substances may still be lower if the removal rate of the parent material is high. For example, sulfamethazine undergoes advanced oxidation treatment and the parent material removal rate reaches 90%, while the mineralization rate is less than 40%. The results of UV/persulfate treatment of ibuprofen and heat-activated persulfate treatment of naproxen in pure water systems show that the removal rate of total organic carbon is significantly lower than that of the parent material. Residual intermediates still have potential ecological risks. If the secondary effluent of a waste water treatment plant undergoes advanced oxidation treatment, the non-mineralized degradation products will also have low concentration and persistence characteristics when entering the environmental water body. Therefore, it is of important significance to test the toxic effects of the waste water on aquatic organisms after treated with advanced oxidation technology.

SUMMARY OF THE INVENTION

Aiming at the above problems, the present invention provides a biological toxicity test method to evaluate the ecological safety of advanced oxidation processes that is simple and objective with good applicability to the ecological risk assessment of waste water from different waste waters sources and various advanced oxidation processes.

The technical solution of the present invention is: a biological toxicity test method for evaluating the ecological safety of an advanced oxidation process, comprising the following steps:

S1: collecting (preparing) a waste water to be tested;

S2: subjecting the waste water and a tap water to an advanced oxidation process, respectively, and setting up a blank control and establishing four groups of experimental pools, namely a waste water control group, a waste water experimental group, a tap water blank group, and a tap water experimental group;

S3: putting Koi (*Cyprinus carpio haematopterus*) into the treated experimental pools;

S4: dissecting, after farming for a period of time, the Koi in each experimental group and extracting the liver to formulate into a homogenate and determining an activity of antioxidative enzymes in the homogenate;

S5: conducting intragroup data comparison for the determined data of the homogenate in each group to obtain an average value of biological indicators of various antioxidative enzymes and the like, plotting a histogram according to the average value of each of the biological indicators in each group, comparing the histogram for each of the biological indicators to evaluate the tested advanced oxidation process.

Further, the waste water in S1 refers to a simulated waste water containing micro-contaminants or a secondary effluent from secondary sewage plants. Heavy polluted waste water may cause death of Koi, such that the test result is inaccurate.

Further, the advanced oxidation process in S2 refers to a hydroxyl (.OH) based or a sulfate radical ($SO_4^-$.) or a chlorine radical (Cl.) based higher oxidation technology, including but not limited to $UV/H_2O_2$, UV/persulfate, $UV/ClO_2$.

Still further, the manner or parameters for treating the waste water by the advanced oxidation process in S2 may be appropriately adjusted according to different advanced oxidation processes.

Still further, in the experimental groups of S2, the collected waste water is divided into a raw waste water and an experimental waste water, the raw waste water is waste water that is not treated, and the experimental waste water is waste water that has been subjected to advanced oxidation process treatment; the tap water is collected and the collected tap water is divided into two portions of a control tap water and a blank tap water, and the control tap water is tap water that has been subjected to advanced oxidation process treatment, and the blank tap water is tap water that is not treated.

Still further, four groups of identical experimental pools are established in S2. Each group of experimental pools is provided with 3 parallel groups. The size of each experimental pool is unified to 30 L. The water temperature of the experimental pool is 18° C. to 22° C. Each experimental pool is provided with an aerator. The first group of the experimental pools is the waste water control group, the second group is the waste water group, the third group is the tap water control group, and the fourth group is the tap water blank group. The four groups of experimental pools have same conditions except the addition of different water quality. 25 L of raw waste water, experimental waste water, control tap water, and blank tap water are sequentially added to the experimental pool of the waste water control group, the waste water experimental group, the tap water control group, and the tap water control group.

Still further, 20 selected Koi are put into each experimental pool in S3 for exposure to poison. The Koi used in the test are those domesticated with tap water and not poisoned by the contaminants. The duration of exposure is 96 h-110 h. During the period of exposure, half water is changed every day with water of same quality to maintain the water quality in a stable condition.

Further, the method in S4 is specifically: the Koi after exposure to poison in each group is dissected and liver is extracted, chopped, and formulated into a homogenate with the liver tissue and physiological saline according to weight (g): volume (mL)=1:9 and the activity of antioxidative enzymes in the homogenate is determined.

Still further, the antioxidative enzyme determined in S4 comprises superoxide dismutase, catalase, and glutathione peroxidase.

Still further, the biological indicators such as the determined enzyme activity described in S4 are determined using a kit, and 5 parallel group assays are set for each sample group.

Further, the intragroup data comparison in S5 is specifically: the data in the three experimental pools in each group of experiments is compared, firstly data anomalies in a certain experimental pool is eliminated, and then all data in the rest experimental pools are subjected to removal of abnormal data, and the remaining data are rearranged; the out-of-group comparison method is specifically: the statistics of the data after rearranging of each experimental group are collected, and then the average value of all the data in each experimental group is taken, the abnormal data is eliminated first, and then the normal data is averaged, so that data processing can more accurately evaluate the tested advanced oxidation process.

The beneficial effects of the present invention are:

(1) By applying the test scheme of the present invention, a biological toxicity test method for evaluating the ecological safety of an advanced oxidation process, the obtained toxicity test results can effectively evaluate the ecotoxicity removal effect of advanced oxidation processes on waste water, and further understand the applicability of the advanced oxidation process.

(2) There are four groups of experiments in the exposure experiment. Each group of experiments has 3 parallel groups. Multiple experiment pools are more conducive to the exclusion of abnormal data and accidental errors. In the data analysis process of the method, the abnormal data is eliminated after intragroup comparison, and the histogram is plotted after out-of-group comparison. The present test method is critical in thinking and the result is more accurate, and the experimental data is more conducive to analysis.

EMBODIMENTS OF THE INVENTION

Example 1

Figure 1:
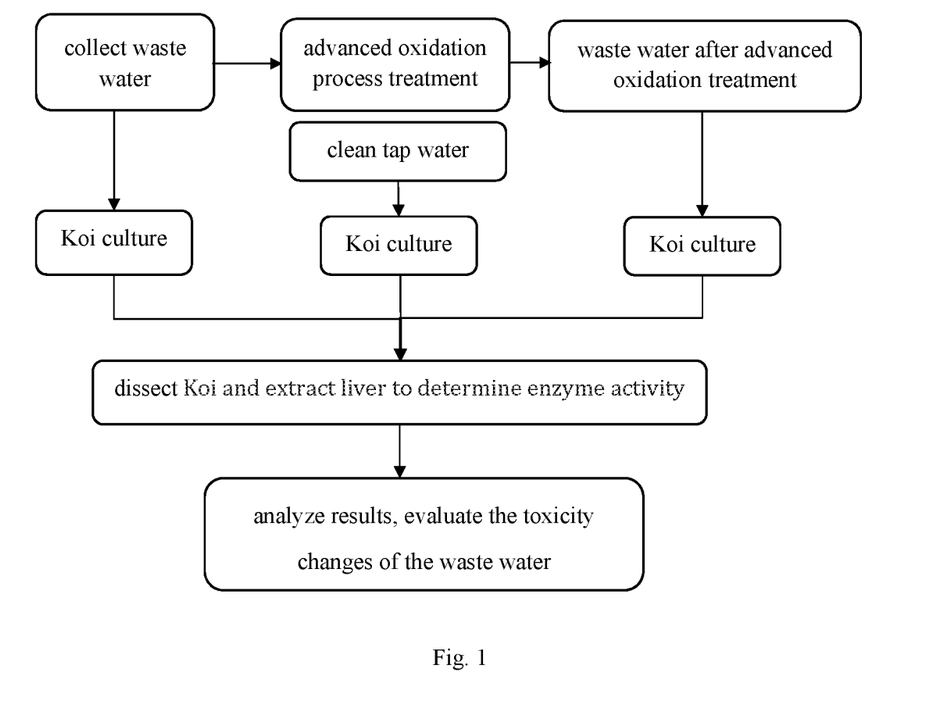
FIG. 1 is an experimental flow chart of the present invention.

In this embodiment, the waste water containing a non-steroid anti-inflammatory drug and a $UV/H_2O_2$ process are taken as subjects and specifically described. As shown in FIG. 1, the biological toxicity test method for evaluating the ecological safety of the $UV/H_2O_2$ process comprises the following steps:

S1: the waste water to be determined was collected (prepared), resulting in inaccurate test results. Four groups of experimental pools were established, namely a waste water control group, a waste water experimental group, a tap water blank group, a tap water experimental group, and 1 μM non-steroid anti-inflammatory drug ibuprofen was added to the four experimental groups.

S2: an $H_2O_2$ solution was added to the waste water experimental group and the tap water control group so that the molar ratio of $H_2O_2$ to the non-steroid anti-inflammatory drug was 1:100, and the reaction solution was irradiated with UV for 30 minutes. Four groups of identical experimental pools were established. Each group of the experimental pools was provided with 3 parallel groups. The size of each experimental pool was unified to 30 L. The temperature of the experimental pool water was 18° C. to 22° C. Each experimental pool was provided with an aerator. The first group of the experimental pools was the waste water control group, the second group was the waste water group, the third group was the tap water control group, and the fourth group was the tap water blank group. The four groups of experimental pools had same conditions except the addition of different water quality. 25 L of raw waste water, experimental waste water, control tap water, and blank tap water were sequentially added to the experimental pool of the waste water control group, the waste water experimental group, the tap water control group, and the tap water control group.

S3: 20 selected Koi were put into each experimental pool for exposure to poison. The Koi used for the test were those domesticated with tap water and not poisoned by the contaminants. The exposure time was 96 hours. During the period of exposure, half water was changed every day with water of same quality to maintain the water quality in a stable condition.

S4: each group of Koi after exposure in the step S3 was dissected and extracted for liver tissue, chopped, and formulated to a homogenate with the liver tissue and physiological saline according to weight (g): volume (mL)=1:9. Antioxidative enzyme activity was determined in the homogenate. The antioxidative enzymes determined comprised superoxide dismutase, catalase, and glutathione peroxidase.

S5: the data in the three experimental pools in each group of experiments was compared, firstly data anomalies in a certain experimental pool was eliminated, and then all data in the rest experimental pools were subjected to removal of abnormal data, and the remaining data were rearranged; the out-of-group comparison method is specifically: the statistics of the data after rearranging of each experimental group were collected, and then the average value of all the data in each experimental group was taken, the abnormal data was eliminated first, and then the normal data was averaged. Then FIG. 2a, FIG. 2b, and FIG. 2c were plotted sequentially according to the average values of catalase (CAT), glutathione peroxidase (GPx), and superoxide dismutase (SOD) in each group of experiments. The histograms of various antioxidative enzymes were evaluated for the selected UV/$H_2O_2$ process.

Figure 2A:
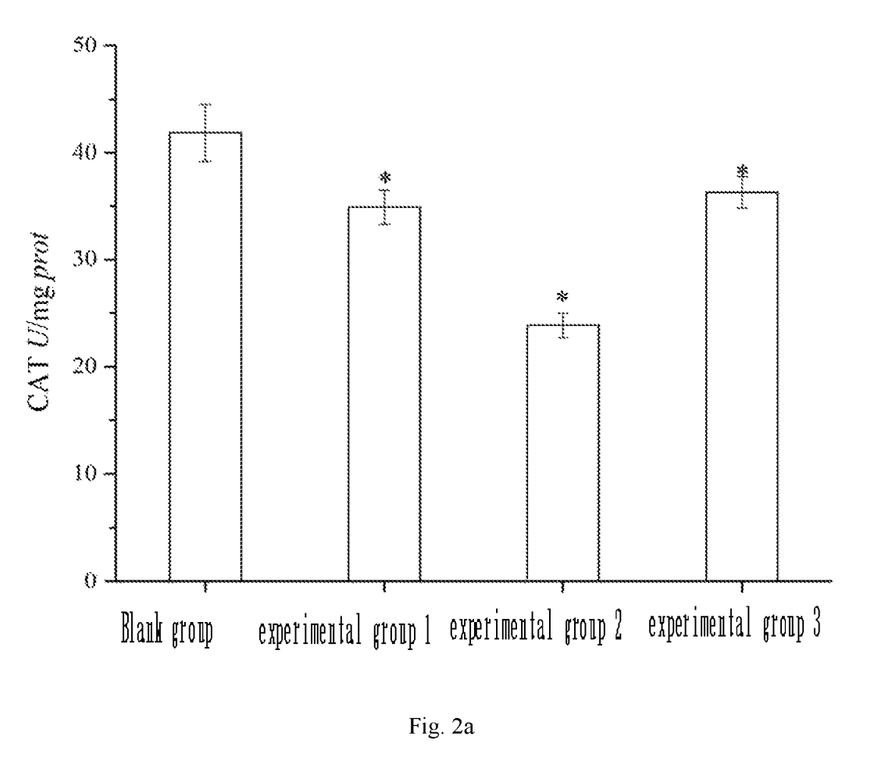
FIG. 2a is a histogram of catalase (CAT) activity of each experimental group in Example 1 of the present invention.
Figure 2B:
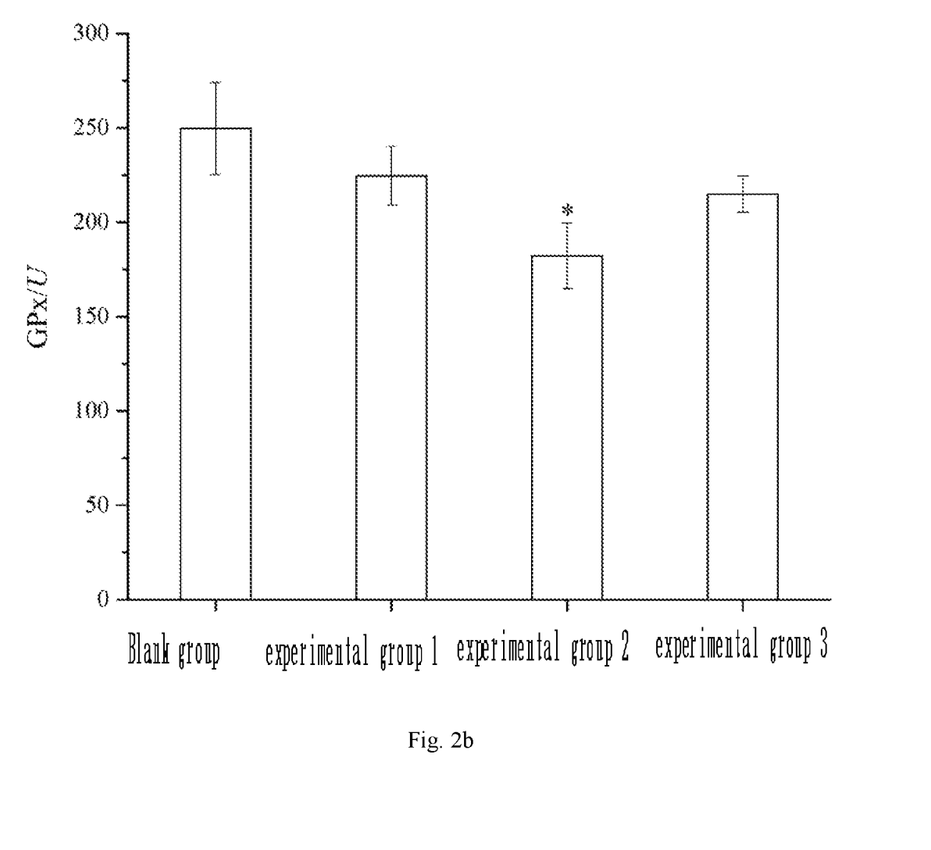
FIG. 2b is a glutathione peroxidase (GPx) activity in Example 1 of the present invention.
Figure 2C:
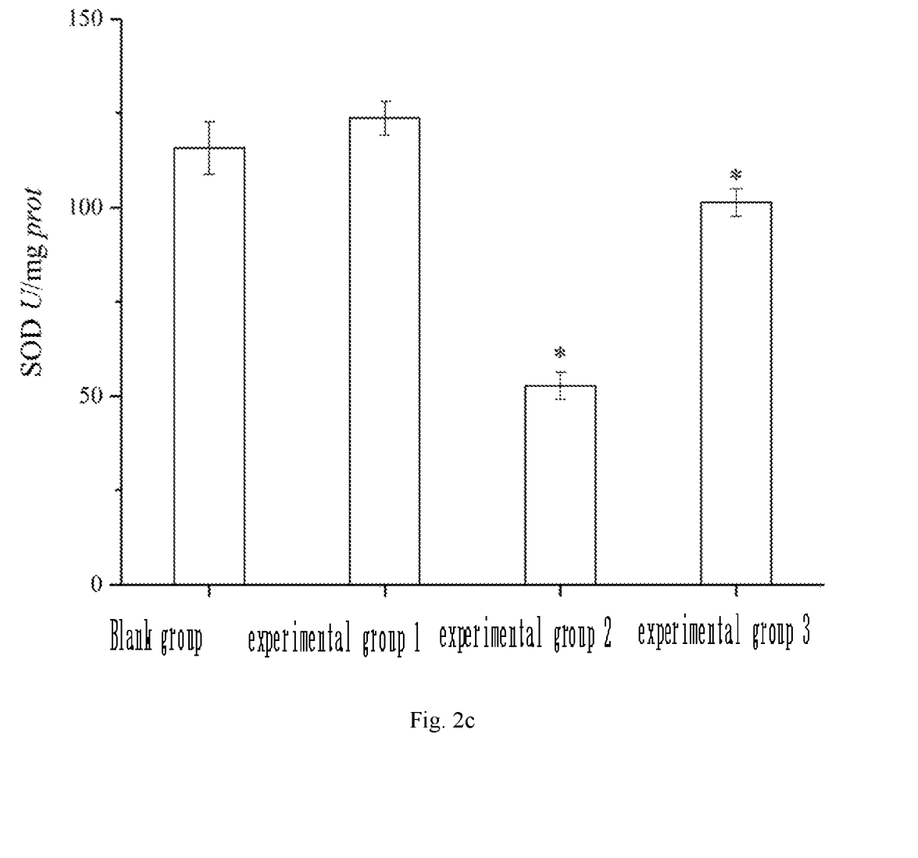
FIG. 2c is a superoxide dismutase (SOD) activity of each experimental group in Example 1 of the present invention.

Among them, FIG. 2a, FIG. 2b, and FIG. 2c are the results of the determination of superoxide dismutase (SOD), glutathione peroxidase (GPx), and catalase (CAT) activity in each experimental group. The entry of harmful substances into living organisms will result in the accumulation of active oxygen, and the 3 antioxidative enzymes of SOD, CAT and GPx act synergically to eliminate the harmful effects of reactive oxygen species in the body. SOD is firstly involved in the scavenging of reactive oxygen species, which may catalyze the decomposition of superoxide anions into $H_2O_2$. This is the first step in the antioxidant defense mechanism, followed by CAT and GPx intervention to convert the $H_2O_2$ produced into $H_2O$ and $O_2$. CAT mainly attaches to peroxisomes, and its main function is to reduce $H_2O_2$ produced by metabolism of long-chain fatty acids on peroxisomes, while CAT plays a dual role in the catalytic reduction of $H_2O_2$ and lipid peroxides. The different reaction mechanisms of CAT and GPx represent two pathways for active oxygen removal. Generally, when organisms are under mild reactive oxygen stress, SOD and CAT activities are increased to accelerate the removal of reactive oxygen species in the body; while severe and prolonged active oxygen stress may exceed the balance regulation ability of the organism's antioxidant defense system, such that the activity of SOD and CAT are reduced, which results in accumulation of reactive oxygen species in the living body and leads to oxidative damage in the organism.

It is known from FIGS. 2a, 2b, and 2c, the activities of SOD, GPx, and CAT in experimental group 2 and experimental group 3 are inhibited, and the SOD, GPx, and CAT activities in experimental group 2 are more significantly suppressed than those in experimental group 3. This shows that the toxicity of the waste water with non-steroid anti-inflammatory drug increases after UV/$H_2O_2$ treatment. The SOD activity of experimental group 1 is higher than that of the fourth group, namely the blank group. The GPx activity is lower than that of the blank group but there is no significant difference, indicating that the oxidant $H_2O_2$ in UV/$H_2O_2$ also produces oxidative stress on the koi.

Example 2

Effect of the duration of exposure to poison:

Example 1 was taken as a reference, and four control groups were set up. The rest of the conditions were the same. The duration of exposure to poison was shown in Table 3:

TABLE 1

| Duration of exposure in each group | |
|---|---|
| Group | Duration (h) |
| Example 1 | 98 |
| Comparative Example 1 | 96 |
| Comparative Example 2 | 110 |
| Comparative Example 3 | 90 |
| Comparative Example 4 | 112 |

The test results show that the results of Comparative Example 1 and Comparative Example 2 are basically the same as that of Example 1, and there is no difference. The difference between the enzyme activity values of the experimental groups in Comparative Example 3 and the blank control group is small. It may be that the exposure time is not enough, the amount of active oxygen accumulation is not enough, and the damage to the Koi is not obvious; deaths to some of the Koi occur in Comparative Example 4, which may be due to the exposure time is too long.

The results show that when the duration of exposure is in the range of 96-110 h, the test data has higher sensitivity and better accuracy. When the duration of exposure is less than 96 hours, the test data has lower sensitivity, and the accuracy is not high. When the duration of exposure is longer than 110 hours, some of the Koi may die, leading to inaccurate test results.

Example 3

The difference between the present example and Example 1 lies in that the present example takes a papermaking waste water and an ozone combined oxidation process as the subjects, and all the other parameters and methods are the same as those in Example 1.

Figure 3A:
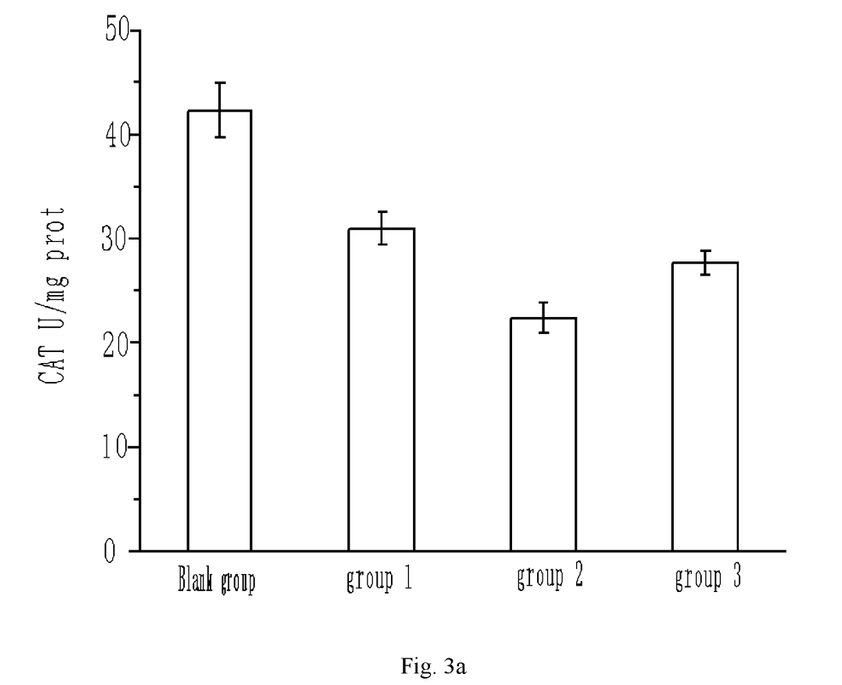
FIG. 3a is the catalase (CAT) activity of each experimental group in Example 3 of the present invention.
Figure 3B:
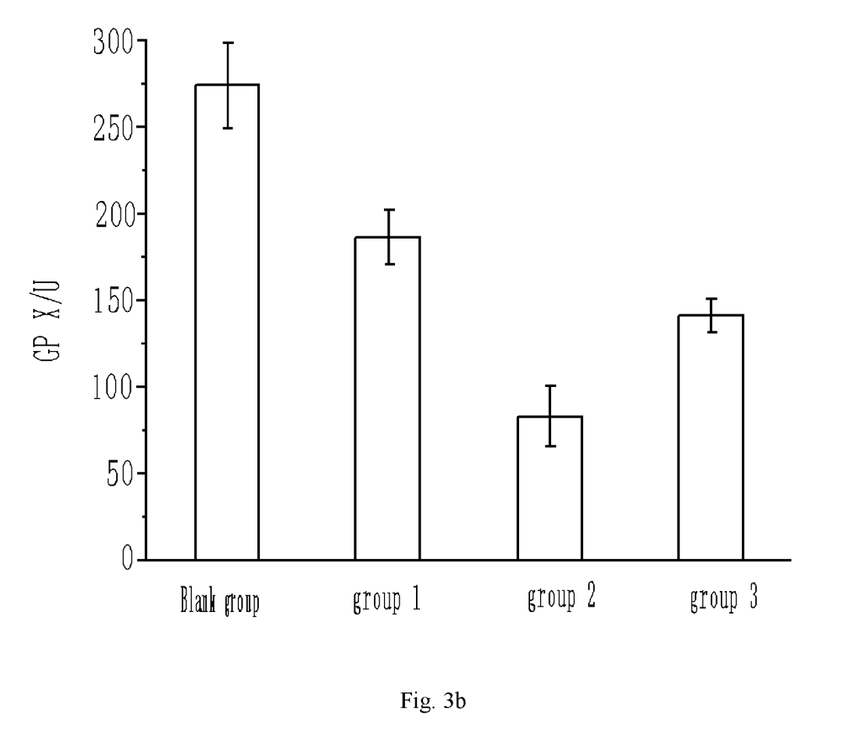
FIG. 3b is the glutathione peroxidase (GPx) activity of each experimental group in Example 3 of the present invention.
Figure 3C:
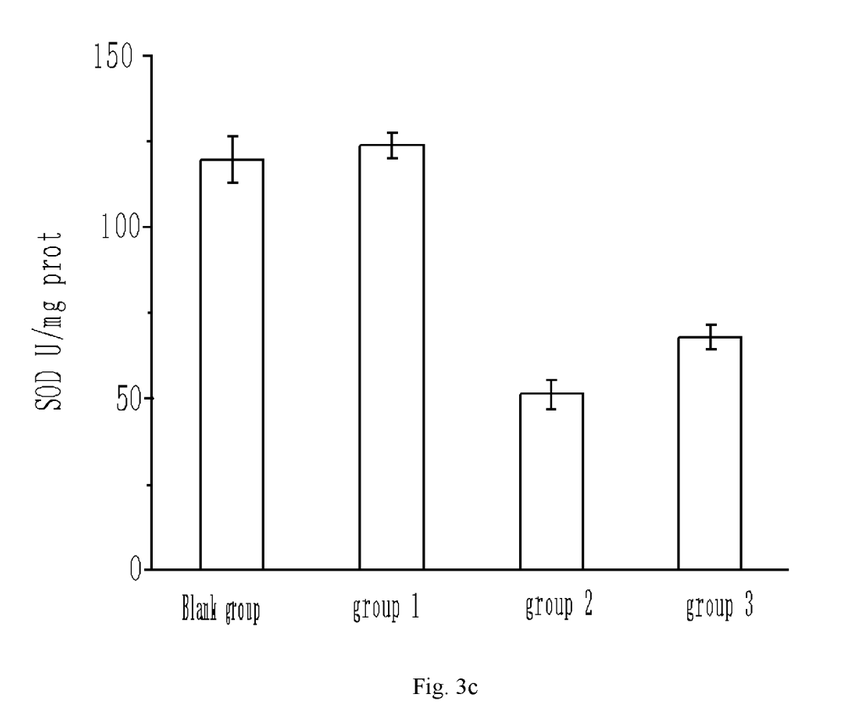
FIG. 3c is the superoxide dismutase (SOD) activity of each experimental group in Example 3 of the present invention.

The test results are somewhat different from those of Example 1, as shown in FIGS. 3a, 3b, and 3c. It is known from FIG. 3a, FIG. 3b, and FIG. 3c, the activities of SOD, GPx, and CAT in experimental group 2 and experimental group 3 are inhibited, and the SOD, GPx, and CAT activities of the experimental group 2 are more significantly suppressed than those of the experimental group 3. The results show that the toxicity of papermaking waste water is increased after the ozone combined oxidation process. The SOD activity of experimental group 1 is higher than that of the fourth group, namely the blank group. The GPx activity is lower than that of the blank group but there is no significant difference, indicating that the oxidant $H_2O_2$ in the ozone combined oxidation process also produces oxidative stress on the Koi. It may be due to the fact that there is a certain difference between each pollutant species in the papermaking waste water and Example 1, but the histograms of various antioxidative enzymes in each of the experimental groups are basically consistent with those of Example 1.

The results show that the method of the present invention is also applicable to the evaluation of the treatment results of papermaking waste water by the ozone combined oxidation process.

Example 4

The difference between the present example and Example 1 lies in that the present example takes a VC waste water and a wet oxidation process as the subjects, and all other parameters and methods are the same as those in Example 1.

Figure 4A:
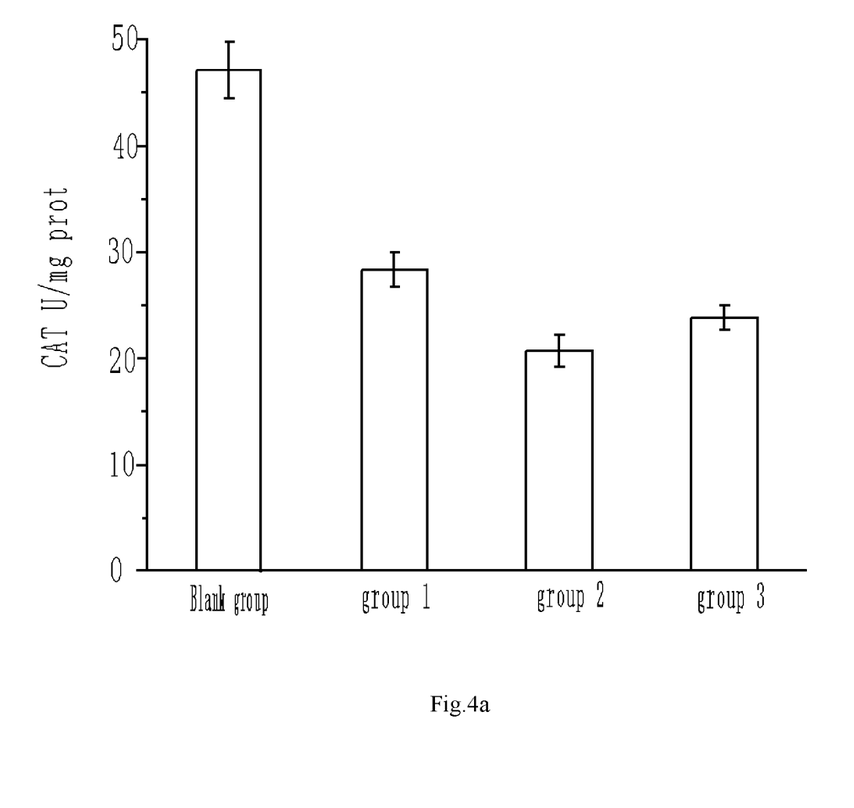
FIG. 4a is the catalase (CAT) activity of each experimental group in Example 4 of the present invention.
Figure 4B:
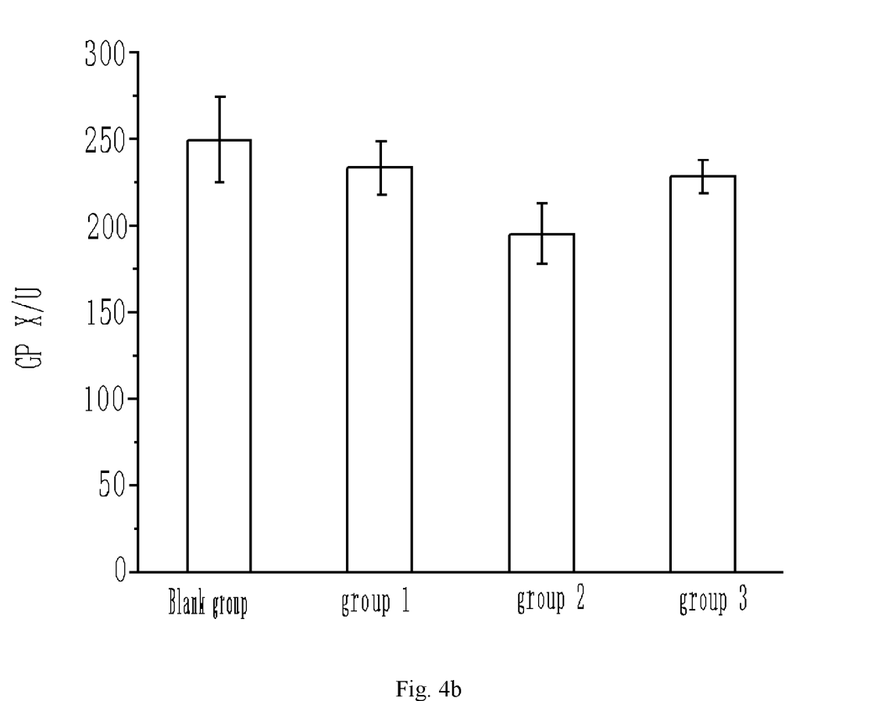
FIG. 4b is the glutathione peroxidase (GPx) activity of each experimental group in Example 4 of the present invention.
Figure 4C:
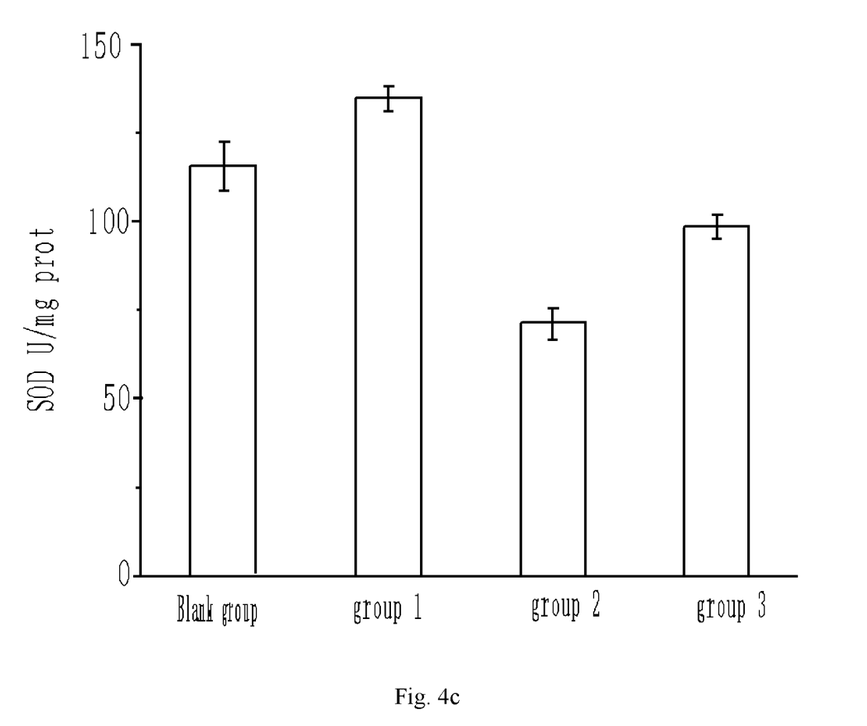
FIG. 4c is the superoxide dismutase (SOD) activity of each experimental group in Example 4 of the present invention.

The test results are somewhat different from those of Example 1, as shown in FIGS. 4a, 4b and 4c. It is known from FIG. 4a, FIG. 4b and FIG. 4c, the activities of SOD, GPx and CAT in experimental group 2 and experimental group 3 are inhibited, and the SOD, GPx, and CAT activities of the experimental group 2 are more significantly suppressed than those of the experimental group 3. The results show that the toxicity of the VC waste water after the wet oxidation process is increased. The SOD activity of experimental group 1 is higher than that of the fourth group, namely the blank group. The GPx activity is lower than the blank group but there is no significant difference, indicating that the oxidant $H_2O_2$ in the wet oxidation process also produces oxidative stress on the Koi. It may be due to the fact that there is a certain difference between each pollutant species in the VC waste water and Example 1, but the histograms of various antioxidative enzymes in each of the experimental groups are basically consistent with those of Example 1.

The results show that the method of the present invention is also applicable for the evaluation of the treatment results of VC waste water in a wet oxidation process.

The above description of the embodiments is only for the purpose of understanding the method of the present invention and its core idea. It is noted that those skilled in the art can make several improvements and modifications to the present invention without departing from the principle of the present invention, and these improvements and modifications will also fall within the protection scope of the present invention.

We claim:

1. A method for evaluating ecological safety of an advanced oxidation process, comprising the following steps:
    (S1) Koi domestication: collecting tap water and dechlorinating the tap water by aeration for three days, selecting healthy Koi fish of 10±1 cm in length and keeping them in dechlorinated tap water for 10 days with a death rate lower than 3%, wherein the Koi fish is *Cryprinus carpio haematopterus*;
    (S2) exposure of the Koi fish to poison:
    (1) collecting waste water containing micro-contaminants or a secondary effluent from secondary sewage plants, dividing the collected waste water into two fractions, wherein the waste water in one fraction is subjected to an advanced oxidation process treatment and used as experimental waste water, wherein the waste water in another fraction is not subjected to the treatment and used as raw waste water, and wherein the advanced oxidation process treatment is $UV/Na_2S_2O_8$, $UV/H_2O_2$, or $UV/ClO_2$;
    (2) collecting tap water and dechlorinating the tap water as indicated in step S1, dividing dechlorinated tap water into two fractions, wherein the dechlorinated tap water in one fraction is subjected to the advanced oxidation process treatment and used as experimental tap water, and wherein the dechlorinated tap water in another fraction is not subjected to the treatment and used as raw tap water;
    (3) establishing three experimental groups and setting up one blank control group, wherein each group is provided with three parallel sub-groups, and each parallel sub-group is conducted with a fish tank, the size of which is unified to 50 L; wherein the first experimental group is a waste water control group with the experimental tap water added to each fish tank, the second experimental group is a waste water group with the raw waste water added to each fish tank, the third experimental group is a waste water experimental group with the experimental waste water added to each fish tank, and the blank control group is the tap water experimental group with the raw tap water added to each fish tank; wherein the three experimental groups and the blank control group have same conditions except for different water qualities; and wherein 1 μM non-steroid anti-inflammatory drug ibuprofen is added to each fish tank of the blank group, the first, second, and third experimental groups; and
    (4) putting 10 Koi fish, selected and domesticated with the raw tap water according to step S1, into each fish tank of the three experimental groups and the blank control group for exposure to poison for a period of 96-110 hours, wherein during the period of exposure to poison, half water in each fish tank is changed every day with water of same quality to maintain water quality in a stable condition;
    (S3) detection of activities of antioxidative enzymes: dissecting, after the exposure to poison according to step S2, the Koi fish in each group and extracting the liver, and then chopping and formulating the liver into a homogenate of liver tissues with a physiological saline according to a ratio of weight (g): volume (mL)=1:9; and determining the activities of antioxidative enzymes in the homogenate, wherein the antioxidative enzymes determined comprise superoxide dismutase, catalase, and glutathione peroxidase; and
    (S4) analysis of the enzyme activities of the Koi fish: statistically analyzing the enzyme activity results of step S3 to generate an average value of the enzyme activities for each of the three experimental groups and the blank control group, wherein the average value in each experimental or blank control group is compared to determine toxicity changes of waste water before and after the advanced oxidation process treatment; thereby evaluating the ecological safety of the advanced oxidation process.

2. The method for evaluating ecological safety of the advanced oxidation process according to claim 1, wherein a water temperature of each fish tank is in a range from 20° C. to 25° C., and each fish tank is provided with an aerator.

3. The method for evaluating ecological safety of the advanced oxidation process according to claim 1, wherein a ratio of male and female ratio of Koi fish put in each fish tank is 1:1.

4. The biological toxicity test method for evaluating ecological safety of the advanced oxidation process according to claim 3, wherein the Koi fish is of 9 cm in length and the time period for the exposure to poison is 96 hours.

* * * * *